United States Patent [19]

Umezawa et al.

[11] 3,939,143

[45] Feb. 17, 1976

[54] 1-N-ISOSERYLKANAMYCINS AND THE PRODUCTION THEREOF

[75] Inventors: Hamao Umezawa; Kenji Maeda, both of Tokyo; Shinichi Kondo, Yokohama; Sumio Umezawa, Tokyo, all of Japan

[73] Assignee: Zaidan Hojin Biseibutsu Kagaku Kenkyu Kai, Tokyo, Japan

[22] Filed: May 1, 1974

[21] Appl. No.: 466,053

[30] Foreign Application Priority Data
May 15, 1973  Japan.............................. 48-53151
Aug. 29, 1973  Japan.............................. 48-96176

[52] U.S. Cl............................. 260/210 K; 424/180
[51] Int. Cl.²......................................... C07A 15/04
[58] Field of Search ............................. 260/210 K

[56] References Cited
UNITED STATES PATENTS 3,032,547  5/1962  Rothrock et al................ 260/210 K
3,753,973  8/1973  Umezawa et al................. 260/210 K
3,781,268  12/1973  Kawaguchi et al.............. 260/210 K

OTHER PUBLICATIONS

Morrison and Boyd, "Organic Chemistry" Allynl and Bacon Inc., Boston, 1970, p. 1101.

*Primary Examiner*—Johnnie R. Brown
*Assistant Examiner*—Cary Owens
*Attorney, Agent, or Firm*—James C. Haight

[57] ABSTRACT

1-N-isoseryl derivatives of kanamycin A, kanamycin B and 3',4'-dideoxykanamycin B are now synthesized, which are new and useful compounds active against gram-negative and gram-positive bacteria and also against drug-resistant strains of these bacteria. The production of the 1-N-isoserylkanamycins is made by reacting isoserine with the 1-N-amino group of kanamycin with the functional amino group(s) being protected, following by removal of the amino-protecting groups and by chromatographic separation of the desired 1-N-isoserylation product.

11 Claims, No Drawings

1-N-ISOSERYLKANAMYCINS AND THE PRODUCTION THEREOF

This invention relates to 1N-isoserylkanamycin A, 1-N-isoserylkanamycin B and 1-N-isoseryl-3',4'-dideoxykanamycin B which are new and useful compounds active against gram-negative and gram-positive bacteria and also against drug-resistant strains of these bacteria. This invention further relates to a process for the production of these 1-N-isoseryl derivatives of the kanamycins.

Kanamycin A (hereinafter called merely kanamycin) and kanamycin B are well known aminoglycosidic antibiotics which have widely been used as valuable chemotherapeutic agents. Unfortunately, however, some drug-resistant strains of bacteria which are resistant to the action of these known aminoglycosidic antibiotics have occurred in recent years. Accordingly, the mechanism of resistance of these drug-resistant bacteria to the known aminoglycosidic antibiotics has been studied. For instance, one of the present inventors, H. Umezawa et al, has found that some strains of gram-negative bacteria carrying R factor, *Staphylococcus aureus* and *Pseudomonas aeruginosa* isolated from patients, are resistant to kanamycins and that these kanamycin-resistant strains have as a mechanism of resistance the production of an enzyme capable of phosphorylating the 3'-hydroxyl group of kanamycins and inactivating the kanamycins by the action of the phosphotransferase (see "Science" Vol. 157, page 1,559 (1967).

On the basis of these findings, H. Umezawa et al prepared 3'-deoxykanamycin and 3',4'-dideoxykanamycin B which are not susceptible to the action of the phosphotransferase as described in the "Journal of Antibiotics" Ser. A, Vol. 24, pages 274–275 (1971) and Vol. 24, pages 485–487 (1971). 3'-Deoxykanamycin and 3',4'-dideoxykanamycin B are actually effective against the abovementioned kanamycin-resistant strains but have further been found to be inactive against other kinds of kanamycin-resistant strains such as *Escherichia coli* JR66/W677 into which has been transferred the R factor from clinically isolated Klebsiella. H. Umezawa et al have found that the latter kind of kanamycin-resistant strains have a mechanism of resistance in that they produce an enzyme capable of adenylylating the 2''-hydroxyl group of the kanamycin or 3',4'-dideoxykanamycin B molecule with ATP (adenosine triphosphate) and inactivating kanamycin and 3',4'-dideoxykanamycin B by the action of this nucleotidyltransferase; see the "Journal of Antibiotics" Vol. 24, pages 911–913 (1971) and "Journal of Antibiotics" Vol. 25, page 492 (1972).

On the other hand, it is known that butirosin B which is an aminoglycosidic antibiotic produced by a Bacillus species is active against some kanamycin- and ribostamycin-resistant bacteria. Butirosin B has been identified as 1-N-[(S)-4-amino-2-hydroxy-n-butyryl]-ribostamycin; see the "Tetrahedron Letters" Vol. 28, page 2,125 and pages 2,617–2,630 (1971) and German Offenlegungsschrift No. 1,914,527. By comparison of the antibacterial activity of ribostamycin with that of butirosin B, we have found that the (S)-4-amino-2-hydroxybutyryl substituent on the 1-amino group of the butirosin B molecule has an important role in enabling the substituted ribostamycin to be active against both ribostamycin resistant and -sensitive strains and that the presence of the (S)-4-amino-2-hydroxybutyryl substituent at the 1-amino group of the butirosin B molecule can inhibit the action of the nucleotidyltransferase produced by the kanamycin-resistant strains. From the above findings and in view of the molecular structure of the kanamycins, we presumed there would be a possibility that there could be produced in new and useful derivatives of the kanamycins in which the 1-amino group is modified by introduction of a bulky substituent thereon to bring about steric hindrance of the 2''-hydroxyl group and thereby to render the kanamycin insusceptible to the action of the inactivating enzymes of the kanamycin-resistant bacteria. With this presumption, we have made further study to synthetize new derivatives of kanamycins which are usefully effective not only against the gram-negative and gram-positive bacteria but also against the drug-resistant bacteria. As a result, we have now found that acylation of the 1-amino group of kanamycin, kanamycin B and 3',4'-dideoxykanamycin B with isoserine, either in the racemic form or in the form of the L-isomer or in the form of the D-isomer, gives new and useful kanamycin derivatives which exhibit a useful antibacterial activity against the gram-negative and gram-positive bacteria as well as against the drug-resistant bacteria.

An object of this invention is, therefore, to provide new kanamycin derivatives which show useful antibacterial activity even against the kanamycin-resistant bacteria. A particular object of this invention is to provide as such new and useful kanamycin derivatives, 1-N-isoserylkanamycin, 1-N-isoserylkanamycin B and 1-N-isoseryl-3',4'-dideoxykanamycin B. Another object of this invention is to provide a process for the production of these new 1-N-isoseryl derivatives of kanamycins which is carried out in a facile way and gives a favorable yield of the desired product. Other objects of this invention will be clear from the following description.

We have now succeeded in obtaining 1-N-isoserylkanamycin, 1-N-isoserylkanamycin B and 1-N-isoseryl-3', 4'-dideoxykanamycin B by acylating kanamycin, kanamycin B and 3',4'-dideoxykanamycin B, respectively, at the 1-amino group thereof with isoserine while the amino groups other than said 1-amino group are partially or wholly blocked by a known amino-protecting group, removing the amino-protecting groups from the resulting acylation products and then isolating the desired product in a chromatographic manner. It has further been found that the 1-N-isoserylkanamycins so synthetized exhibit a usefully high antibacterial activity against the bacteria sensitive to kanamycin, kanamycin B and 3',4'-dideoxykanamycin B, as well as against the kanamycin-resistant bacteria, including *Pseudomonas aeruginosa*.

According to a first aspect of this invention, therefore, there is provided a compound selected from the group consisting of 1-N-isoserylkanamycin, 1-N-isoserylkanamycin B and 1-N-isoseryl-3',4'-dideoxykanamycin B, which are generically represented by the following general formula:

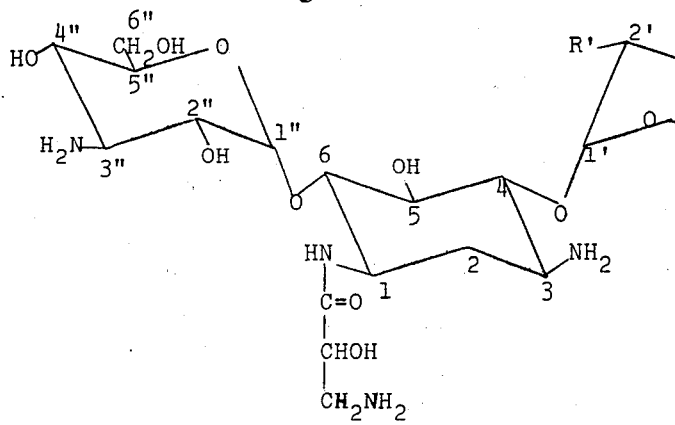

wherein R is a hydroxyl group or a hydrogen atom and R' is amino group or a hydroxyl group, provided that when R is a hydrogen atom, R' is the amino group, and the pharmaceutically acceptable acid-addition salts thereof. As the isoseryl moiety in the molecule of the compound of the above general formula (I) may be either in the DL-form or in the L-form or in the D-form, it may be noted that in accordance with this invention the term 1-N-isoserylkanamycin includes 1-N-DL-isoserylkanamycin, 1-N-L-isoserylkanamycin and 1-N-D-isoserylkanamycin; that the term 1-N-isoserylkanamycin B includes 1-N-DL-isoserylkanamycin B, 1-N-L-isoserylkanamycin B and 1-N-D-isoserylkanamycin B; and that the term 1-N-isoseryl-3',4'-dideoxykanamycin B includes 1-N-DL-isoseryl-3',4'-dideoxykanamycin B, 1-N-L-isoseryl-3',4'-dideoxykanamycin B and 1-N-D-isoseryl-3',4'-dideoxykanamycin B.

1-N-isoserylkanamycin corresponds to the compound of the above general formula (I) where R and R' are each the hydroxyl group. 1-N-isoserylkanamycin B corresponds to the compound of the general formula (I) where each R is the hydroxyl group and R' is the amino group. 1-N-isoseryl-3',4'-dideoxykanamycin B corresponds to the compound of the general formula (I) where each R is the hydrogen atom and R' is the amino group.

Examples of the pharmaceutically acceptable acid-addition salts of the compounds of the above-mentioned general formula (I) according to this invention include the hydrochloride, sulfate, phosphate, acetate, maleate, fumarate, succinate, tartrate, oxalate, citrate, methanesulfonate, ethanesulfonate and the like.

1-N-DL-isoserylkanamycin has the following physical, chemical and biological properties: This compound is a substance in the form of a colorless crystalline powder with a decomposition point of 174°–177°C, $[\alpha]_D^{25}$ +89° (c 0.65, water). This substance gives a single spot positive to the ninhydrin reaction at Rf 0.27 on thin layer chromatography in silica gel (available under a trade name "ART 5721," a product of E. Merck, West Germany) using a solvent system of 4:1:2:1, methanol-chloroform-28% aqueous ammonia-water as the development solvent (whereas kanamycin shows Rf 0.39 under the same conditions). This substance also gives a single spot at Rf 0.08 on thin layer chromatography with the same silica gel when using a solvent system of 4:5:2:5, butanol-ethanol-chloroform-17% aqueous ammonia as the development solvent (while kanamycin shows Rf 0.11 in the latter case). The ultra-violet absorption spectrum of this substance in water shows only the end absorption, and infra-red absorption of this substance in a potassium bromide pellet shows main absorption peaks at 3,400, 2,950, 1,650, 1,560, 1,490, 1,390, 1,340, 1,150 and 1,030 $cm^{-1}$, from which the existence of an amide linkage —CONH— in the molecule of the substance can be confirmed. This substance exhibits a high antibacterial activity not only against various gram-negative and gram-positive bacteria which are sensitive to kanamycins, but also against the drug-resistant strains of Escherichia coli and Pseudomonas aeruginosa. This substance is of a low toxicity to animals and man, as shown by the fact that it exhibits an $LD_{50}$ value of more than 200 mg/kg upon intravenous injection of this compound in mice.

1-N-L-isoserylkanamycin is a substance in the form of a colorless crystalline powder with a decomposition point of 184°–187°C, $[\alpha]_D^{24}$ +74° (c 0.85, water). 1-N-D-isoserylkanamycin is a substance also in the form of a colorless crystalline powder with a decomposition point of 184°–188°C, $[\alpha]_D^{24}$ +82° (c 0.33, water). The other properties (including antibacterial activity and toxicity) of 1-N-L-isoserylkanamycin and 1-N-D-isoserylkanamycin are observed to be the same as those of 1-N-DL-isoserylkanamycin.

1-N-DL-isoserylkanamycin B has the following physical, chemical and biological properties: This compound is a substance in the form of a colorless crystalline powder with a decomposition point of 179°–184°C, $[\alpha]_D^{26}$ +86° (c 0.72, water). This substance gives a single spot positive to the ninhydrin reaction at Rf 0.09 on thin layer chromatography with silica gel (available under a trade name "ART 5721", a product of E. Merck, West Germany) using a solvent system of 4:5:2:5 butanol-ethanol-chloroform-17% aqueous ammonia as the development solvent (whereas kanamycin B shows Rf 0.16 under the same conditions). The ultra-violet absorption spectrum of this substance in water shows only the end absorption, and the infra-red absorption spectrum of this substance in a potassium bromide pellet shows main absorption peaks from which the existence of an amide linkage in the molecule of this compound can be confirmed. The NMR spectrum reveals that this substance is a compound in which kanamycin B and DL-isoserine are bonded with each with in a molar ratio of 1:1. This substance exhibits a high antibacterial activity not only against various gram-negative and gram-positive bacteria which are sensitive to kanamycins, but also against the drug-resistant strains of Escherichia coli and Pseudomonas aeruginosa. This substance is of a low toxicity to animals and man as shown by the fact that it exhibits an $LD_{50}$ value of more than 100 mg/kg upon intravenous injection of this compound in mice.

1-N-DL-isoseryl-3',4'-dideoxykanamycin B has the following physical, chemical and biological properties: This compound is a substance in the form of a colorless crystalline powder with a decomposition point of 174°–175°C, $[\alpha]_D^{26}$ +82° (c 0.32, water). This substance gives a single spot positive to the ninhydrin reaction at Rf 0.17 on thin layer chromatography with silica gel (available under a trade name "ART 5721", a product of E. Merck, West Germany) using a solvent system of 4:5:2:5 butanol-ethanol-chloroform-17% aqueous ammonia as the development solvent (whereas 3',4'-dideoxykanamycin B shows Rf 0.26 under the same conditions). The ultra-violet absorption spectrum of this substance in water shows only the end absorption, and the infra-red absorption spectrum of this substance in a potassium bromide pellet shows main absorption peaks from which the existence of an amide linkage in the molecule of this compound can be confirmed. The NMR spectrum reveals that this substance is a compound in which kanamycin B and DL-isoserine are bonded with each with in a molar ratio of 1:1. This substance also exhibits a high antibacterial activity not only against various gram-negative and gram-positive bacteria which are sensitive to kanamycins, but also against the drug-resistant strains of *Escherichia coli* and *Pseudomonas aeruginosa*. This substance is of a low toxicity to animals and man as shown by the fact that it exhibits an LD$_{50}$ value of more than 100 mg/kg upon intravenous injection of this compound in mice.

The minimum inhibitory concentrations (mcg/ml) of 1-N-DL-isoserylkanamycin, 1-N-DL-isoserylkanamycin B and 1-N-DL-isoseryl-3',4'-dideoxykanamycin B against various microorganisms were determined according to the serial dilution method using nutrient agar medium at 37°C, the estimation being effected after 18 hours incubation. For comparison purposes, the minimum inhibitory concentrations of kanamycin, kanamycin B and 3',4'-dideoxykanamycin B were also determined in the same manner and under the same conditions as mentioned above.

The antibacterial spectra of 1-N-DL-isoseryl-kanamycin (abbreviated as 1-IS-KM), 1-N-DL-isoseryl-kanamycin B (abbreviated as 1-IS-KMB) and 1-N-DL-isoseryl-3',4'-dideoxykanamycin B (abbreviated as 1-IS-DKB) are shown in the following table together with those of kanamycin (abbreviated as KM), kanamycin B (abbreviated as KMB) and 3',4'-dideoxykanamycin B (abbreviated as DKB).

| Test organisms | Minimum Inhibitory Concentration (mcg/ml) | | | | | |
|---|---|---|---|---|---|---|
| | KM | 1-IS-KM | KMB | 1-IS-KMB | DKB | 1-IS-DKB |
| Staphylococcus aureus FDA 209P | 0.78 | 0.78 | 0.39 | 1.56 | <0.20 | 0.78 |
| Staphylococcus aureus Smith | <0.20 | 0.20 | <0.20 | <0.20 | <0.20 | <0.20 |
| Staphylococcus aureus Terajima | <0.20 | <0.20 | <0.20 | <0.20 | <0.20 | <0.20 |
| Sarcina lutea PCI 1001 | 6.25 | 3.12 | 1.56 | 6.25 | 6.25 | 1.56 |
| Bacillus anthracis | <0.20 | <0.20 | <0.20 | <0.20 | <0.20 | <0.20 |
| Bacillus subtilis PCI 219 | <0.20 | <0.20 | <0.20 | <0.20 | <0.20 | <0.20 |
| Bacillus subtilis NRRL B-558 | <0.20 | <0.20 | <0.20 | <0.20 | <0.20 | <0.20 |
| Bacillus cereus ATCC 10702 | 1.56 | 0.78 | 0.78 | 1.56 | 0.78 | 1.56 |
| Corynebacterium bovis 1810 | 3.13 | 1.56 | 1.56 | 1.56 | 3.13 | 0.78 |
| Mycobacterium smegmatis ATCC 607 | 0.78 | 0.39 | 0.78 | 0.78 | 0.39 | <0.20 |
| Shigella dysenteriae JS 11910 | 6.25 | 3.13 | 3.13 | 6.25 | 1.56 | 3.13 |
| Shigella flexneri 4b JS 11811 | 6.25 | 3.13 | 3.13 | 3.13 | 1.56 | 3.13 |
| Shigella sonnei JS 11746 | 3.13 | 1.56 | 1.56 | 6.25 | 0.78 | 3.13 |
| Salmonella typhosa T-63 | 0.39 | 0.78 | 0.20 | 0.78 | <0.20 | 0.78 |
| Salmonella enteritidis 1891 | 0.78 | 0.78 | 1.56 | 0.78 | 1.56 | 0.39 |
| Proteus vulgaris OX 19 | 0.78 | 0.39 | 0.78 | 0.78 | <0.20 | 0.20 |
| Klebsiella pneumoniae PCI 602 | 0.78 | 0.39 | 0.78 | 0.78 | 0.39 | 0.39 |
| Klebsiella pneumoniae 22 No. 3038 | >100 | 1.56 | >100 | 6.25 | 100 | 1.56 |
| Escherichia coli NIHJ | 1.56 | 1.56 | 0.78 | 3.13 | 0.39 | 1.56 |
| Escherichia coli K-12 | 1.56 | 0.78 | 0.78 | 1.56 | 0.78 | 1.56 |
| Escherichia coli K-12 ML 1629 | >100 | 1.56 | >100 | 3.13 | 0.78 | 1.56 |
| Escherichia coli K-12 ML 1630 | >100 | 1.56 | >100 | 3.13 | 0.78 | 1.56 |
| Escherichia coli K-12 ML 1410 | 1.56 | 1.56 | 0.78 | 1.56 | 1.56 | 1.56 |
| Escherichia coli K-12 ML 1410 R81 | >100 | 1.56 | >100 | 3.13 | 1.56 | 1.56 |
| Escherichia coli LA290 R55 | 100 | 1.56 | 12.5 | 1.56 | 50 | 1.56 |
| Escherichia coli LA290 R56 | 12.5 | 0.78 | 3.13 | 0.78 | 12.5 | 0.39 |
| Escherichia coli LA290 R64 | 12.5 | 0.78 | 3.13 | 0.78 | 6.25 | 0.39 |
| Escherichia coli W677 | 1.56 | 0.78 | 0.39 | 0.78 | 0.20 | 0.78 |
| Escherichia coli JR66/W677 | >100 | 3.13 | >100 | 12.5 | 50 | 3.13 |
| Pseudomonas aeruginosa A3 | 50 | 3.13 | 50 | 6.25 | 1.56 | 3.13 |
| Pseudomonas aeruginosa No.12 | 25 | 0.78 | 12.5 | 6.25 | 0.78 | 1.56 |
| Pseudomonas aeruginosa TI-13 | >100 | 3.13 | 100 | 6.25 | 1.56 | 3.13 |
| Pseudomonas aeruginosa GN315 | >100 | >100 | >100 | 50 | >100 | 12.5 |
| Pseudomonas aeruginosa 99 | >100 | 6.25 | >100 | 6.25 | 3.13 | 3.13 |

The 1-N-DL(or -L- or -D-)-isoserylkanamycin, 1-N-DL(or -L- or -D-)-isoserylkanamycin B and 1-N-DL(or -L- or -D-)-isoseryl-3',4'-dideoxykanamycin B, that is, the new compounds of the general formula (I) according to this invention, are all of low toxicity to animals and man, as shown by the fact that they have LD$_{50}$ values of more than 100 mg/kg upon intravenous injection of the compounds in mice. In addition, the new compounds of this invention exhibit a high antibacterial activity against various gram-positive and gram-negative bacteria, including the kanamycin-resistant strains, so that the new compounds of this invention may be useful in treatment of infections by gram-positive and gram-negative bacteria. The compounds of this invention may be administered orally, intraperitoneally, intravenously, subcutaneously or intramuscularly using any pharmaceutical form known to the art for such administration and in a similar manner to the kanamycins. For instance, the compounds of the formula (I) of this invention may be administered orally using any pharmaceutical form known to the art for such oral administration. Examples of pharmaceutical forms for oral administration are powders, capsules, tablets, syrups, and the like. Suitable dosages of the compounds for the effective treatment of bacterial infections are in a range of 0.25–2 g per person per day when it is given orally. It is preferred that said dose should be orally administered in three to four aliquots per day. The compounds of this invention may also be administered by intramuscular injection at a dosage of 50–200 mg per person two to four times per day. Moreover, the compounds of the invention may be formulated into an ointment for external application which contains the compounds of this invention at a concentration of 0.5–5% by weight in mixture with a known ointment base such as polyethylene glycol.

The compounds of the formula (I) according to this invention, that is to say, 1-N-isoserylkanamycin, 1-N-isoserylkanamycin B and 1-N-isoseryl-3',4'-dideoxykanamycin B, principally may be produced from kanamycin, kanamycin B and 3',4'-dideoxykanamycin B, respectively, which are represented by the following general formula:

has been blocked by the amino-protecting group with the 1-amino group remaining in the free state, because the preparation of such an amino-protected derivative is relatively easier and simpler owing to the fact that the 6'-amino group is the most reactive among all the amino groups of the starting compound (II) and is hence capable of being protected preferentially by the amino-protecting group while keeping the other amino groups unblocked. Kanamycin B and 3',4'-dideoxykanamycin B also contain the 2'-amino group in the molecule thereof, and the reactivity of the 2'-amino group is lower than that of the 6'-amino group but higher than that of the other amino groups. Accordingly, it is also feasible to prepare such an amino-

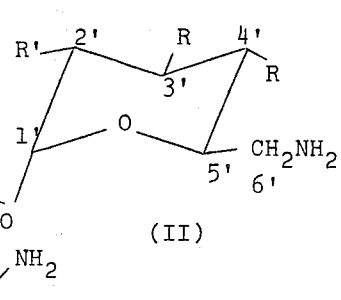

wherein R is hydroxyl group or a hydrogen atom and R' is a amino or hydroxyl group, provided that when R is an hydrogen atom, R' is the amino group, by reacting a starting compound of the above general formula (II) selectively at the 1-amino group thereof with isoserine of the formula:

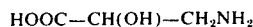

HOOC—CH(OH)—CH$_2$NH$_2$ (III)

in a manner known in the prior art acylation of amino groups. The starting material kanamycin contains four amino groups per molecule, while kanamycin B and 3',4'-dideoxykanamycin B contain five amino groups per molecule thereof. In order to achieve the production of the new compound of the formula (I) according to this invention, it is required that only the 1-amino group of the starting compound of the formula (II) should selectively be acylated with isoserine without acylation of the other amino groups. It will be obvious that the desired new compound of the formula (I) would be obtained in a best yield if the isoserine reactant of the formula (III) is reacted with an amino-protected derivative of the starting compound of the formula (II) in which all the amino groups other than the 1-amino group (namely, the 6'-, 3- and 3''-amino groups of kanamycin or the 6'-, 2'-, 3- and 3''-amino groups of kanamycin B and 3',4'-dideoxykanamycin B) have been blocked by a known amino-protecting group while the 1-amino group remains free. The preparation of such an amino-protected derivative of the starting compound of the formula (II) is possible, but needs a very complicated method comprising a number of reaction steps. In this situation, it is rather preferred to prepare an amino-protected derivative of the starting compound of the formula (II) in which merely the primary 6'-amino group of the starting compound (II)

protecting derivative of kanamycin B or 3',4'-dideoxykanamycin B with either only the 6'-amino group or both the 6'-amino and 2'-amino groups protected by the amino-protecting group.

When the so-prepared amino-protected derivative of the compound (II) in which the 6'-amino group (and possibly also the 2'-amino group with kanamycin B and 3',4'-dideoxykanamycin B) has been blocked is reacted with isoserine (III) of which the amino group may preferably be blocked with an amino-protecting group, there may be formed a mixture of different acylation products comprising the desired 1-N-mono-isoseryl product in which only the 1-amino group has been acylated with the isoserine, as well as such undesired mono- or multiisoseryl products of which at least one of the amino groups other than the 1-amino group and other than the blocked 6'-amino group (possibly also the blocked 2'-amino group) has been acylated with the isoserine, respectively. When these mixed acylation products so formed are treated so as to remove the amino-protecting groups therefrom, there may be produced mixed isoseryl derivatives of the starting compound (II) comprising the desired 1-N-mono-isoseryl product of the formula (I) as well as the undesired mono- or multi-isoseryl products from which the amino-protecting groups have already been liberated. The desired 1-N-mono-isoseryl product (I) may be isolated from said mixed isoseryl derivatives in a chromatographic manner, separately from the other undesired isoseryl products which exhibit lower antibacterial activity against the drug-resistant and -sensitive bacteria than the desired product (I).

According to a second aspect of this invention, therefore, there is provided a process for the production of the compounds 1-N-isoserylkanamycin, 1-N-isoserylkanamycin B or 1-N-isoseryl-3',4'-dideoxykanamycin B of the aforesaid general formula (I), which comprises acylating a compound of the general formula:

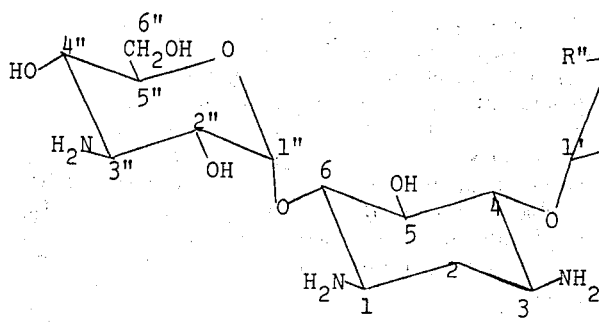 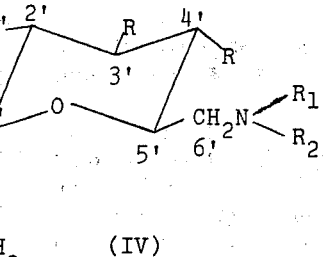

(IV)

wherein R is a hydroxyl group or a hydrogen atom and R'' is the amino group —$NH_2$, an amino group blocked with a known amino-protecting group, or a hydroxyl group, provided that when R is hydrogen, R'' is the amino group or the blocked amino group; $R_1$ is a known amino-protecting group and $R_2$ is a hydrogen atom, or $R_1$ and $R_2$ taken together form a known divalent amino-protecting group, with an isoserine compound (including the racemic form, the L-isomer and the D-isomer) of the formula:

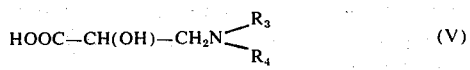

(V)

wherein $R_3$ and $R_4$ are each a hydrogen atom or a known amino-protecting group, or $R_3$ and $R_4$ taken together forms a known divalent amino-protecting group, to produce the mixed acylation products containing the desired intermediate product of the formula:

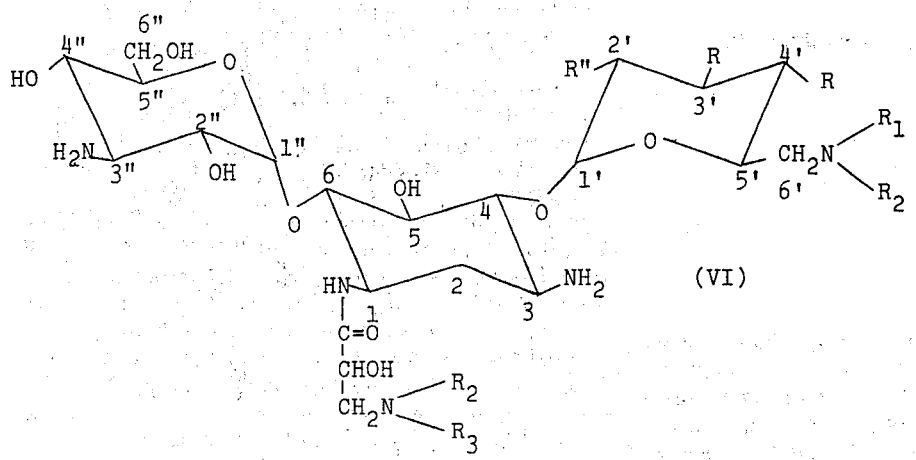

(VI)

wherein R, R'', $R_1$, $R_2$, $R_3$ and $R_4$ are each as defined above, removing the amino-protecting groups from said mixed acylation products, and then isolating the desired compound of the formula (I) out of the mixed acylation products which have been freed from the amino-protecting groups.

To prepare the compound having the amino group protected according to the above formula (IV) which is employed as the starting material in the process of this invention, kanamycin, kanamycin B or 3',4'-dideoxykanamycin B, that is, a compound of the above formula (II), is reacted with a reagent which is known and is commonly used in the conventional synthesis of peptides to introduce a known amino-protecting group. Accordingly, the above-mentioned known amino-protecting groups available in this invention may be any of the amino-protecting groups which are commonly used in the conventional synthesis of peptides, as long as it is capable of being removed readily from the products of the acylation step of the present process by treating the acylation products in a known manner for the removal of the amino-protecting group, without substantially affecting the amide linkage which has been formed between the 1-N-isoseryl radical and the kanamycin moiety of the acylation products.

As suitable examples of the known amino-protecting groups $R_1$, $R_2$, $R_3$ and $R_4$ which are available in this invention, there may be mentioned an alkyloxycarbonyl group such as ethoxycarbonyl, t-butoxycarbonyl a t-amyloxycarbonyl; an cycloalkyloxycarbonyl group such as cyclopentyloxycarbonyl and cyclohexyloxycarbonyl; an aralkyloxycarbonyl group such as benzyloxycarbonyl and p-nitrobenzyloxycarbonyl; an aryloxycarbonyl group such as phenoxycarbonyl and furfuryloxycarbonyl; an acyl group such as o-nitrophenoxyacetyl; and the like. When a pair of the groups $R_1$ and $R_2$ or a pair of the groups $R_3$ and $R_4$ taken together forms a known divalent amino-protecting group, this divalent amino-protecting group may be a phthaloyl group or a salicylidene group and generally an alkylidene or arylidene group of the formula =$CHR_5$ in which $R_5$ is an alkyl group of 1–6 carbon atoms such as methyl, ethyl, propyl, isopropyl, butyl or pentyl, or an aryl group such as phenyl, tolyl, p-methoxyphenyl or o-hydroxyphenyl.

Such known amino-protecting groups as alkyloxycarbonyl, aralkyloxycarbonyl or aryloxycarbonyl groups may be shown by a formula -CO-$OR_6$ in which $R_6$ is an alkyl group of 1–5 carbon atoms such as methyl, ethyl, t-butyl and t-amyl or a cycloalkyl group of 3–6 carbon atoms such as cyclopentyl and cyclohexyl; an aralkyl group such as phenyl alkyl group containing alkyl of 1–4 carbon atoms, for example, benzyl and p-nitrobenzyl; an aryl group such as phenyl or a heterocyclic group such as furfuryl. The preferred amino-protecting groups are t-butoxy and benzyloxy, as these are capable of reacting with the 6'-amino group and possibly also with the 2'-amino group of the compound (II) and being removed from the acylation products most readily.

For the preparation of such an amino-protected compound of the formula (IV) in which the 6'-amino group alone or together with the 2'-amino group has been blocked by a known amino-protecting group of the type -CO-OR$_6$, the antibiotic compound of the formula (II) may be reacted with a substantially equimolar proportion of a chloroformate of the formula:

Cl—CO—OR$_6$ (VII)

or a p-nitrophenyl carbonate of the formula:

p—NO$_2$—C$_6$H$_5$—O—CO—OR$_6$ (VII')

or an N-hydroxysuccinimide ester of the formula:

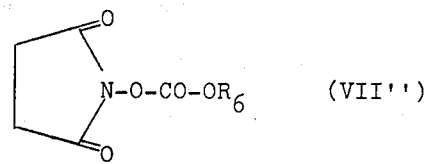
(VII'')

or an azidoformate of the formula:

N$_3$—CO—OR$_6$ (VII''')

or a 4,6-dimethylpyrimidyl-2-thiol-carbonate of the formula:

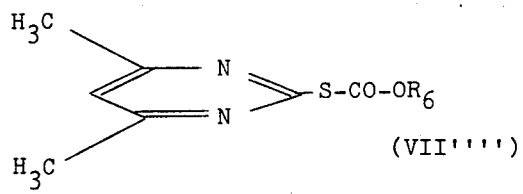
(VII'''')

wherein R$_6$ is as defined above, in a suitable solvent such as water, ethanol, acetone or a mixture thereof under a neutral or basic conditions in a manner known in the prior art of synthesis of peptides. The reaction products so obtained consist of a mixture of various amino-protected derivatives of the compound (II) comprising the main proportion of compounds where only the 6'-amino group has been blocked by the group —CO—OR$_6$, as well as minor proportions of compounds where the 6'-amino group and at least one of the other amino groups have been blocked by the group —CO—OR$_6$, and so on. By subjecting this mixture of reaction products to a chromatographic separation using a cation-exchange resin containing carboxylic functions, for example, a copolymer of methacrylic acid with divinylbenzene (available under a trade name "Amberlite" IRC 50 or "Amberlite" CG 50, a product of Rohm Haas, U.S.A., in the form of the ammonium salt), there may be isolated the starting compound (IV) in which the 6'-amino group alone or together with the 2'-amino group has been blocked by the amino-protecting group of the type —CO—OR$_6$.

For the protection of such amino-protected compounds of the formula (IV) in which the 6'-amino group alone or together with the 2'-amino group has been blocked by a known, divalent amino-protecting group of the alkylidene or arylidene type =CHR$_5$, the antibiotic compound of the formula (II) may be alkylidenated or arylidenated by reacting with a substantially equimolar proportion of an aldehyde of the formula:

OHC—R$_6$ (VIII)

wherein R$_6$ is as defined above, in a manner known in the production of Schiff bases. Suitable aldehyde (VIII) for this purpose include acetaldehyde, anisaldehyde, tolualdehyde, p-nitrobenzaldehyde and salicyl aldehyde. In this way, there may be obtained the mixed alkylidenation or arylidenation products, which may be subjected to a chromatographic separation using a cation-exchange resin as stated above to isolate the starting compound (IV) in which the 6'-amino group alone or together with the 2'-amino group has been blocked by the amino-protecting group of the type =CHR$_5$.

For instance, 6'-N-t-butoxycarbonylkanamycin may be prepared in a high yield by reacting kanamycin in solution in a mixture of pyridine, water and triethylamine with a 1 to 3 molar proportion of t-butoxycarbonyl azide added dropwise thereto under agitation, stirring the admixture at ambient temperature overnight, concentrating the reaction mixture to dryness in vacuo and then purifying the solid residue in a column chromatography with a cation-exchange resin such as Amberlite CG 50 (NH$_4$ form), while recovering the unreacted kanamycin. Moreover, 2',6'-di-N-t-butoxycarbonylkanamycin B or 3',4'-dideoxykanamycin B may be prepared in a high yield, for example, by reacting kanamycin B or 3',4'-dideoxykanamycin B in solution in a mixture of pyridine, water and triethylamine with a 2-3 molar proportion of t-butoxycarbonyl azide added dropwise thereto under agitation, stirring the admixture at ambient temperature overnight, concentrating the reaction mixture to dryness in vacuo, and then purifying the solid residue in column chromatography with a cation-exchange resin such as Amberlite CG 50 (NH$_4$ form). When this preparation procedure is repeated with 2 molar proportions or less of t-butoxycarbonyl azide, there may be obtained 6'-N-t-butoxycarbonyl-kanamycin B or 3',4'-dideoxykanamycin B in a high yield. 6'-N-t-butoxycarbonyl-kanamycin B or 3',-4'-dideoxykanamycin B once isolated may also be converted into the 2',6'-di-N-t-butoxycarbonyl derivative by further reacting with 1 to 2 molar proportions of t-butoxycarbonyl azide in a similar manner. The compounds of the formula (IV) prepared in the above procedures may be employed as a starting compound in the process of this invention without purification.

In acylating the starting compound (IV) with the isoserine compound (V) in accordance with the process of this invention, the compound (IV) is reacted with the isoserine compound (V) in a manner known for the acylation which is used commonly in the conventional synthesis of amides. Thus, the compound (IV) may be acylated by condensing with the isoserine compound (V) in a solution in dimethylformamide, acetone or tetrahydrofuran under ice-cooling and in the presence of a dehydrating agent such as dicyclohexylcarbodiimide. The isoserine employed may either be in the racemic form or in the optically active forms. When an optically active isoserine, for example, (L)-isoserine or (D)-isoserine, is used the product of the process of this invention is then as biologically active that of the racemic form. Of course, the isoserine compound (V) may also be used in the form of its reactive derivative such as the acid chloride, the mixed acid anhydride, the active esters or the azide derivative thereof. Thus, it is feasible that the isoserine compound (V) is at first reacted with N-hydroxysucciimide in the presence of dicyclohexylcarbodiimide to prepare its active ester of the formula:

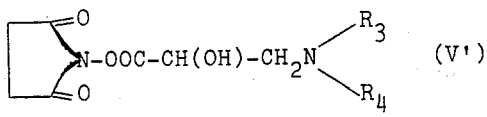

which is, in turn, reacted with the compound (IV) for the N-acylation of the latter compound. It is preferred that the compound (IV) should be reacted with 0.5 to 3 molar proportions of the active ester form of the isoserine compound (V') in a reaction medium consisting of water and an organic solvent such as dimethoxyethane. Of the isoserine compound (V) or its active ester form (V') which is used as the acylating agent in the process of this invention, it is preferred to use a form of the isoserine compound (V) in which the amino-protecting groups $R_3$ and $R_4$ are of the same nature as that of the amino-protecting groups for the $R_1$, $R_2$ and $R''$ present in the starting compound (IV) employed.

In the process of this invention, acylation of the compound (IV) with the isoserine compound (V) or (V') gives the mixed acylation products which are usually composed of a mixture of the desired 1-N-monoisoseryl product and the otherwise undesired mono-N-isoseryl products as well as the undesired multi-n-isoseryl products.

The mixed acylation products so produced may then be treated so as to remove the remaining amino-protecting groups therefrom, that is to say, convert the remaining amino-protecting groups into hydrogen atoms. Before this removal of the amino-protecting groups, however, it is also possible to separate chromatographically the mixed acylation products, for example, using silica gel, so that the unreacted portion of the compound (IV) employed is removed therefrom.

The removal of the remaining amino-protecting groups from the above-mentioned mixed acylation products which are produced by the acylation step of the present process converts the amino-protecting groups into hydrogen atoms and may be effected in the following different ways known per se. Thus, when the amino-protecting group is an alkyloxycarbonyl group such as t-butoxycarbonyl, an cycloalkyloxycarbonyl group, aryloxycarbonyl group, alkylidene or arylidene group, the removal of this kind of amino-protecting group from the acylation products may be effected by subjecting the acylation products to a moderate hydrolysis treatment with an acid such as aqueous trifluoroacetic acid, aqueous acetic acid or diluted hydrochloric acid. When the amino-protecting group is an aralkyloxycarbonyl group such as benzyloxycarbonyl, the removal of this amino-protecting group may be effected by subjecting the acylation products to a hydrogenolysis treatment in the presence of a palladium-carbon catalyst or to a treatment with hydrogen bromide in acetic acid. The o-nitrophenoxyacetyl amino-protecting group may be removed by a reductive treatment. When the amino-protecting group is phthaloyl, the removal of phthaloyl groups from the acylation products may be achieved by treating the acylation products with hydrazine hydrate in ethanol under heating. When the acylation products contain different kinds of the amino-protecting groups, the acylation products may be subjected to simultaneous or successive treatments to remove the different amino-protecting groups therefrom. For instance, when the acylation products contain the t-butoxycarbonyl group and the benzyloxycarbonyl group as the amino-protecting groups, these groups may be removed simultaneously by treating the acylation products to acidic catalytic hydrogenation with 5% palladium on carbon in 90% trifluoroacetic acid and methanol.

After the removal of the amino-protecting groups from the acylation products is carried out, the mixed acylation products from which the amino-protecting groups have been removed are then subjected to a chromatographic separation to remove the unreacted materials and to isolate the desired compound of the formula (I). The removal of the unreacted materials may be effected by column chromatography with silica gel. The isolation of the desired compound of the formula (I) from the mixed acylation products may be achieved efficiently by subjecting the acylation products to an ion-exchange chromatography using, for example, a cation-exchange resin containing carboxylic functions, such as Amberlite IRC 50 or Amberlite CG 50 (products of Rohm & Haas Co., U.S.A.), a weak cation-exchanger such as CM-Sephadex C-25 (a product of Pharmacia Co., Sweden) or CM-cellulose. The eluate from the chromatographic process is collected in fractions, and the antibacterial activity of these fractions is detected using the sensitive bacteria and resistant bacteria as the test microorganisms. Through this detection of the antibacterial activity of each fraction, it is easy to locate the active fractions containing the desired compound of the formula (I) and to recover this desired compound from the active fractions in a manner known in the prior art production and recovery of the known aminoglycosidic antibiotics.

Moreover, for purposes of the isolation and purification of the desired compound of the formula (I) from the mixed acylation products, we have now found it very effective to utilize a ligand-exchange chromatography using an anion-exchange resin such as Dowex 50W × 2 (H cycle) which has been first associated with a metal salt such as cupric chloride, cobaltous chloride, nickel nitrate, ferric chloride, zinc chloride, cadmium chloride and the like and subsequently treated with ammonia or an amine such as methylamine.

This invention is now illustrated with reference to the following Examples to which this invention is not limited in any way.

EXAMPLE 1

Synthesis of 1-N-DL-isoserylkanamycin a. Preparation of 6'-N-tert-butoxycarbonylkanamycin Kanamycin base (20 g, 41.3 milimoles) was dissolved in 1,600 ml of a mixture of pyridine-water-triethylamine (10:10:1 by volume), to which was then added 5.9 g (41.3 millimoles) of tert-butoxycarbonyl azide. The admixture was agitated for 20 hours at ambient temperature to effect the tert-butoxycarbonylation. The reaction mixture was then concentrated to dryness under reduced pressure to give a solid. This solid was dissolved in water and the aqueous solution was passed into a column of 1,000 ml of a cation-exchange resin consisting essentially of a copolymer of methacrylic acid and divinylbenzene (commercially available as "Amberlite" CG 50, ammonium form) to adsorb the butoxycarbonylation products onto by the resin. The resin column was washed with 5,000 ml of water and then with 5,000 ml of 0.05N aqueous ammonia, and elution was subsequently made with 0.1N aqueous ammonia. Those fractions of the eluate which were positive to the ninhydrin reaction and to the Rydon-Smith reaction and gave a single spot in a high-voltage paper electrophoresis were combined together and concentrated to dryness to yield 10.9 g of a white powder of 6'-N-tert-butoxycarbonylkanamycin (decomposition point 202°–203°C). Yield 45.3%. When the resin column was further eluted with 0.3N aqueous ammonia, the unreacted kanamycin was recovered in a yield of 7.3 g (36.6%).

b. Production of 1-N-DL-isoserylkanamycin

The product of the above stage (a), namely 6'-N-tert-butoxycarbonylkanamycin (633 mg, 1.0 millimole) was dissolved in a mixture of 10 ml of water and 5 ml of dimethoxyethane to which was then added a solution of 303 mg (1.0 millimole) of N-hydroxysuccinimide ester of tert-butoxycarbonyl-DL-isoserine in 5 ml of dimethoxyethane. The mixture was stirred for 21 hours at ambient temperature to effect the acylation. The reaction mixture was concentrated to dryness under reduced pressure to give a solid comprising the acylation products. The solid, without being purified, was dissolved in 5 ml of 90% aqueous trifluoroacetic acid and the solution was allowed to stand at ambient temperature for 45 minutes during which removal of the tert-butoxycarbonyl groups took place. The reaction solution was then concentrated to dryness under reduced pressure to give a solid which was subsequently washed with 40 ml of ethyl ether, affording 1,367 mg of a solid material. This solid material was dissolved in water and the aqueous solution was passed into a column of 25 ml of a cation-exchange resin consisting essentially of a copolymer of methacrylic acid and divinylbenzene (commercially available as "Amberlite" CG 50, ammonium form) to adsorb the acylation products onto the resin. The resin column was washed with water (125 ml) and then eluted with 0.25N aqueous ammonia. The eluate was collected in fractions of 5 ml, and every fraction was tested according to a usual plate test method for its antibacterial activity using the kanamycin-sensitive strain *Bacillus subtilis* PCI 219 and the kanamycin-resistant strain *Escherichia coli* JR66/W677 as the test organisms. Those fractions which showed high antibacterial activity to both the strains were combined and concentrated to dryness under reduced pressure to give 190 mg of a white powder. As this powder was found to still contain impurities on a thin layer chromatography of silica gel (available under a trade name "ART 5721", a product of E. Merck, West Germany) using a solvent system of 4:1:2:1, methanol-chloroform-28% aqueous ammonia-water as the development solvent, this powder was dissolved in a mixture of methanol-chloroform-17% aqueous ammonia (4:1:2 by volume) and the solution was purified by column chromatography of 12 g of silicic acid. Thus, the silicic acid column was eluted with the same solvent mixture and the eluate was collected in 4 ml fractions. Every fraction was tested by silica gel thin layer chromatography, and those fractions which gave a single spot in this thin layer chromatography were combined and concentrated to dryness under reduced pressure to give 97 mg of a colorless crystalline powder of 1-N-DL-isoserylkanamycin A. Yield 17.0%. Decomposition point 174°–177°C, $[\alpha]_D^{25}$ +89° ($c$ 0.65, water).

Elemental analysis—Found: C 43.90, H 7.56, N 11.89%. Calculated for $C_{21}H_{41}N_5O_{13}$: C 44.13, H 7.23, N 12.25%.

EXAMPLE 2

Synthesis of 1-N-DL-isoseryl-3',4'-dideoxykanamycin B a. Preparation of 6'-N-tert-butoxycarbonyl-3',4'-dideoxykanamycin B 3',4'-dideoxykanamycin B base (5 g, 11 millimoles) was dissolved in 555 ml of a mixture of pyridine-water-triethylamine (10:10:1 by volume), to which was then added 1.58 g (11 millimoles) of tert-butoxycarbonyl azide. The admixture was agitated for 18 hours at ambient temperature to effect the tert-butoxycarbonylation. The reaction mixture was then concentrated to dryness under reduced pressure to give a solid. This solid was dissolved in water and the aqueous solution was passed into a column of 300 ml of a cation-exchange resin consisting essentially of a copolymer of methacrylic acid and divinylbenzene (commercially available as "Amberlite" CG 50, ammonium form) to adsorb the butoxycarbonylation products onto the resin. The resin column was washed with 1,500 ml of water and then eluted with 0.2% aqueous ammonia. Those fractions of the eluate which were positive to the ninhydrin reaction and to the Rydon-Smith reaction and also gave a single spot in a high-voltage paper electrophoresis were combined and concentrated to dryness, affording 2.8 g of a white powder of 6'-N-tert-butoxycarbonyl-3',4'-dideoxykanamycin B (decomposition point 136°–140°C). Yield 49%. When the resin column was further eluted with 1% aqueous ammonia, the unreacted 3',4'-dideoxykanamycin B was recovered in a yield of 1.8 g (36%).

b. Production of 1-N-DL-isoseryl-3',4'-dideoxykanamycin B

The product of the above stage (a), namely 6'-N-tert-butoxycarbonyl-3',4'-dideoxykanamycin B (553 mg, 1.0 millimole), was dissolved in 21 ml of a mixture of pyridine-water-triethylamine (10:10:1 by volume), to which was then added 160 mg (1.1 millimoles) of tert-butoxycarbonyl azide. The admixture was stirred at ambient temperature for 23 hours and the reaction mixture was concentrated under reduced pressure to give 757 mg of a faint yellow colored powder mixture of 6'-N-tert-butoxycarbonyl-3',4'-dideoxykanamycin B and 2',6'-di-N-tert-butoxycarbonyl-3',4'-dideoxykanamycin B containing a trace of its positional isomers. This powder, without being purified, was dissolved in a mixture of 10 ml of water and 10 ml of dimethoxyethane, to which was subsequently added a solution of 330 mg (1.1 millimoles) of N-hydroxysuccinimide ester of tert-butoxycarbonyl-DL-isoserine in 5 ml of diemthoxyethane. The mixture was stirred for 24 hours at ambient temperature to effect the acylation. The reaction mixture was concentrated to dryness under reduced pressure to give a solid comprising the acylation products. This solid was taken up into 5 ml of 90% aqueous trifluoroacetic acid and the solution was allowed to stand at ambient temperature for 30 minutes during which the removal of the tert-butoxycarbonyl groups was effected. The reaction solution was then concentrated to dryness under reduced pressure to give a solid which was subsequently washed with a small volume of ethyl ether, affording 1.66 g of a faintly yellow colored powder. This powder was dissolved in water and the aqueous solution was passed into a column of 25 ml of a cation-exchange resin consisting essentially of a copolymer of methacrylic acid and divinylbenzene "Amberlite" CG 50) (, ammonium form) to adsorb the acylation products adsorbed by the resin. The resin column was washed with water (125 ml) and the eluted with 0.5N aqueous ammonia. The eluate was collected in fractions each of 5 ml, and every fraction was tested according to a usual plate method for its antibacterial activity using the kanamycin-sensitive strain *Bacillus subtilis* PCI 219 and the kanamycin-resistant strain *Escherichia coli* JR66/W677 as the test microorganisms. Those fractions which showed high anti-bacterial activity to both strains were combined and concentrated to dryness under reduced pressure to give 322 mg of a white powder. As this powder was observed to still contain impurities in a silica gel thin layer chromatography, it was purified by column chromatography with 12 g of silicic acid. Thus, the silica gel column containing the adsorbed acylation product was eluted with a mixture of methanol-chloroform-17% aqueous ammonia (4:1:2 by volume) and the eluate was collected in 4 ml fractions. Every fraction was tested by silica gel thin layer chromatography, and those fractions which gave a single spot in this thin layer chromatography were combined and concentrated to dryness under reduced pressure to give 91 mg of a colorless crystalline powder which was identified as 1-N-DL-isoseryl-3',4'-dideoxykanamycin B. Yield 17%. Decomposition point 174°–175°C. $[\alpha]_D^{26}$ +82° ($c$ 0.32, water).

Elemental analysis—Found: C 46.00, H 7.97, N 15.70%. Calculated for $C_{21}H_{42}N_6O_{10}$: C 46.83, H 7.86, N 15.61%.

EXAMPLE 3

Synthesis of 1-N-DL-isoserylkanamycin B a. Preparation of 6'-N-tert-butoxycarbonylkanamycin B Kanamycin B base (4.83 g, 10 millimoles) was dissolved in 100 ml of water, to which was added a solution of 2.40 g (10 millimoles) of tert-butyl 4,6-dimethylpyrimidyl-2-thiol-carbonate in 100 ml of dioxane. The mixture was agitated for 18 hours at ambient temperature to effect the tert-butoxycarbonylation. The reaction mixture was then concentrated to dryness under reduced pressure to give a solid. This solid was dissolved in water and the aqueous solution was passed into a column of 350 ml of a cation-exchange resin consisting essentially of a copolymer of methacrylic acid and divinylbenzene "Amberlite" CG 50, ammonium form) to adsorb the butoxycarbonylation products onto the resin. The resin column was washed with 1,400 ml of water and then eluted with 0.2% aqueous ammonia. Those fractions of the eluate which were positive to the ninhydrin reaction and to the Rydon-Smith reaction and also gave a single spot in a high-voltage paper electrophoresis were combined and concentrated to dryness, affording 2.35 g of a white powder of 6'-N-tert-butoxycarbonylkanamycin B (decomposition point 168°–172°C). Yield 40%. When the resin column was further eluted with 0.6% aqueous ammonia, the unreacted kanamycin B was recovered in a yield of 1.0 g (21%).

b. Production of 1-N-DL-isoserylkanamycin B

The product of the above stage (a), namely 6'-N-tert-butoxycarbonylkanamycin B (584 mg, 1.0 millimole), was dissolved in 21 ml of a mixture of pyridine-water-triethylamine (10:10:1 by volume), to which was then added 160 mg (1.1 millimoles) of tert-butoxycarbonyl azide. The admixture was stirred at ambient temperature for 23 hours and the reaction mixture was concentrated under reduced pressure to give 715 mg of a faintly yellow colored powder mixture of 6'-N-tert-butoxycarbonylkanamycin B and 2',6'-di-N-tert-butoxycarbonylkanamycin B containing a trace of its positional isomers. This powder, without being purified, was dissolved in a mixture of 10 ml of water and 5 ml of dimethoxyethane, to which was subsequently added a solution of 330 mg (1.1 millimoles) of N-hydroxysuccinimide ester of tert-butoxycarbonyl-DL-isoserine in 6 ml of dimethoxyethane. The mixture was stirred for 24 hours at ambient temperature to effect the acylation. The reaction mixture was concentrated to dryness under reduced pressure to give a solid comprising the acylation products. This solid was taken up into 5 ml of 90% aqueous trifluoroacetic acid and the solution was allowed to stand at ambient temperature for 30 minutes during which the removal of the tert-butoxycarbonyl groups was effected. The reaction solution was then concentrated to dryness under reduced pressure to give a solid which was subsequently washed with a small volume of ethyl ether, affording 1.75 g of a faintly yellow colored powder. This powder was dissolved in water and the aqueous solution was passed into a column of 30 ml of a cation-exchange resin consisting essentially of a copolymer of methacrylic acid and divinylbenzene "Amberlite" CG 50 ammonium form) to adsorb the acylation products onto the resin. The resin column was washed with water (150 ml) and then eluted with 0.25N aqueous ammonia. The eluate was collected in fractions each of 6 ml, and every fraction was tested according to a usual plate method for its antibacterial activity using the kanamycin-sensitive strain *Bacillus subtilis* PCI 219 and the kanamycin-resistant strain *Escherichia coli* JR66/W677 as the test microorganisms. Those fractions which showed high anti-bacterial activity to both strains were combined and concentrated to dryness under reduced pressure to give 248 mg of a white powder. As this powder was observed to still contain impurities in a silica gel thin layer chromatography, it was purified by column chromatography with 11 g of silicic acid. Thus, the silica gel column containing the adsorbed acylation product was eluted with a mixture of methanol-chloroform-17% aqueous ammonia (4:1:2 by volume) and the eluate was collected in 4 ml fractions. Every fraction was tested by silica gel thin layer chromatography, and those fractions which gave a single spot in this thin layer chromatography were combined and concentrated to dryness under reduced pressure to give 69 mg of a colorless crystalline powder which was identified as 1-N-DL-isoserylkanamycin B. Yield 12%. Decomposition point 179°–184°C. $[\alpha]_D^{26}$ +86° (c 0.72, water).

Elemental analysis—Found: C 44.52, H 7.18, N 14.92%. Calculated for $C_{21}H_{42}N_6O_{12}$: C 44.20, H 7.41, N 14.73%.

EXAMPLE 4

Synthesis of 1-N-DL-isoseryl-3',4'-dideoxykanamycin B a. Preparation of 6'-N-benzyloxycarbonyl-3',4'-dideoxykanamycin B 13.53 g (30 millimoles) of 3',4'-dideoxykanamycin (abbreviated as DKB) base was dissolved in 135 ml of water, and to this solution was added dropwise 5.61 g (33 millimoles) of benzyloxycarbonyl chloride over 1 hour under stirring and under ice-cooling (0°–5°C). After the adddition, the mixture was further stirred for 1 hour at ambient temperature and filtered to remove the precipitate. The filtrate was washed with 135 ml of ethyl ether. The aqueous phase was neutralized by addition of aqueous ammonia and then concentrated under reduced pressure. The concentrated solution was passed through a column of 480 ml of a cation-exchange resin consisting essentially of a copolymer of methacrylic acid and divinylbenzene "Amberlite CG 50", (the ammonium form) to effect adsorption of the benzyloxycarbonylated DKB by the resin. The resin column was washed with water (1,920 ml) and then eluted with 0.1N aqueous ammonia. 960 ml of the first running of the eluate was discarded, and the subsequently running fraction of the eluate amounting to 780 ml was collected, concentrated and freeze-driedd to give 5.43 g of a colorless powder of 6'-N-benzyloxycarbonyl DKB, mp. 113°–115°C (with decomposition under foaming). Yield 31%.

b. Synthesis of 1-N-DL-isoseryl-3',4'-dideoxykanamycin B

6'-N-benzyloxycarbonyl-3',4'-dideoxykanamycin B (1 g, 1.62 millimoles) was dissolved in a mixture (85 ml) of pyridine-water-triethylamine (10:10:1 by volume), to which was added tert-butoxycarbonyl azide (256 mg, 1.78 millimoles). The admixture was stirred at ambient temperature for 21 hours and the reaction mixture was concentrated under reduced pressure to give 1.27 g of a yellowish powder mixture of 6'-N-benzyloxycarbonyl-3',4'-dideoxykanamycin B and 2'-N-tert-butoxycarbonyl-6'-N-benzyloxycarbonyl-3',4'-dideoxykanamycin B containing a trace of its positional isomers. This powder, without being purified, was dissolved in a mixture of 5 ml of water and 5 ml of dimethoxyethane, to which was subsequently added a solution of 623 mg (1.78 millimoles) of N-hydroxysuccinimide ester of benzyloxycarbonyl-DL-isoserine in 20 ml of dimethoxyethane. The mixture was stirred for 24 hours at ambient temperature. The reaction mixture was concentrated to dryness under reduced pressure to give a solid comprising the acylation products. This solid was dissolved in a mixture of 90% aqueous trifluoroacetic acid (13 ml), methanol (9 ml) and water (1 ml), and hydrogenated with 5% palladiumcarbon (640 mg) as the catalyst at atmospheric pressure for 5 hours to simultaneously remove the two kinds of N-protecting groups. After removing the catalyst by filtration, evaporation of the solution gave a colorless powder. The powder was subsequently processed in the same purification procedure as in Example 2 (b), affording 1-N-DL-isoreryl-3',4'-dideoxykanamycin B in an 18% yield.

EXAMPLE 5

Synthesis of 1-N-DL-isoserylkanamycin B a. Preparation of 6'-N-benzyloxycarbonylkanamycin B Kanamycin B base (5.8 g, 12 millimoles) was dissolved in 116 ml of water, and to the resulting solution was addded dropwise 2.04 g (12 millimoles) of benzyloxycarbonyl chloride over 1 hour under ice-cooling and stirring. After the addition, the mixture was stirred for 2 hours at ambient temperature. The reaction mixture was filtered to remove the precipitate deposited, and the filtrate was washed with 116 ml of ethyl ether. The aqueous phase was neutralized with aqueous ammonia and then concentrated under reduced pressure. The concentrated solution was then passed into a column of 240 ml of a cation-exchange resin made of a copolymer of methacrylic acid and divinylbenzene "Amberlite CG 50", ammonium form) to adsorb the 6'-N-benzyloxycarbonylated kanamycin B onto the resin. The resin column was then washed with water (960 ml) and subsequently eluted with 0.1N aqueous ammonia. Those fractions of the eluate which were positive to the Rydon-Smith reaction and gave a single spot in high-voltage paper electrophoresis were collected, combined and concentrated to dryness to afford 2.7 g of a white powder of 6'-N-benzyloxycarbonylkanamycin B. Yield 37%.

b. Synthesis of 1-N-DL-isoserylkanamycin B

Butoxycarbonylation of 6'-N-benzyloxycarbonylkanamycin B with tert-butoxycarbonyl azide, acylation with N-hydroxysuccinimide ester of tert-benzyloxycarbonyl-DL-isoserine, removal of N-protecting groups by catalytic hydrogenation in acidic solution and purification by column chromatography in the same manner as in Example 4 (b) afforded 1-N-DL-isoserylkanamycin B in a 17% yield.

EXAMPLE 6

Synthesis of 1-N-L-isoserylkanamycin

6'-N-tert-butoxycarbonylkanamycin (316 mg, 0.5 millimoles) was dissolved in a mixture of 5 ml of water and 2.5 ml of dimethoxyethane, and to the resulting solution was added a solution of 225 mg (0.7 millimoles) of N-hydroxysuccinimide ester of tert-butoxycarbonyl-L-isoserine in 2.5 ml of dimethoxyethane. The admixture was subsequently processed in the same manner as in Example 1 (b), affording 48 mg of 1-N-L-isoserylkanamycin. Yield 17%.

EXAMPLE 7

Synthesis of 1-N-D-isoserylkanamycin

6'-N-tert-butoxycarbonylkanamycin (10.5 mg, 0.18 millimoles) was dissolved in a mixture of 2.5 ml of water and 1.25 ml of dimethoxyethane, and to the resulting solution was added a solution of 55 mg (0.18 millimoles) of N-hydroxysuccinimide ester of tert-butoxycarbonyl-D-isoserine in 1.25 ml of dimethoxyethane. The admixture was subsequently processed in the same manner as in Example 1 (b), affording 19 mg of 1-N-D-isoserylkanamycin. Yield 18%.

EXAMPLE 8

Synthesis of 1-N-L-isoserylkanamycin B

6'-N-tert-butoxycarbonylkanamycin B (117 mg, 0.2 millimoles) was dissolved in a mixture (4 ml) of pyridine-water-triethylamine (10:10:1 by volume), to which was added tert-butoxycarbonyl azide (32 mg, 0.22 millimoles). The admixture was stirred at ambient temperature for 23 hours and the reaction mixture was concentrated to dryness under reduced pressure. The residue, without being purified, was dissolved in a mixture of water (2 ml) and dimethoxyethane (2 ml) and to the resulting solution was added a solution of 66 mg (0.22 millimoles) of N-hydroxysuccinimide ester of tert-butoxycarbonyl-L-isoserine in 1 ml of dimethoxyethane. The admixture was subsequently processed in the same manner as in Example 3 (b), affording 1-N-L-isoserylkanamycin B in a 16% yield. Decomposition point 189°–194°C.

EXAMPLE 9

Synthesis of 1-N-D-isoserylkanamycin B

6'-N-tert-butoxycarbonylkanamycin C (58 mg, 0.1 millimole) was dissolved in a mixture (2 ml) of pyridine-water-triethylamine (10:10:1 by volume), to which was added tert-butoxycarbonyl azide (16 mg, 0.11 millimoles). After stirring for 23 hours, the reaction mixture was concentrated to dryness under reduced pressure. The residue, without being purified, was dissolved in a mixture of water (1 ml) and dimethoxyethane (1 ml) and to the resulting solution was added a solution of 33 mg (0.11 millimoles) of N-hydroxysuccinimide ester of tert-butoxycarbonyl-D-isoserine in 0.5 ml of dimethoxyethane. The admixture was subsequently processed in the same manner as in Example 3 (b), affording 1-N-D-isoserylkanamycin B in a 15% yield. Decomposition point 188°–194°C.

EXAMPLE 10

Synthesis of 1-N-L-isoseryl-3',4'-dideoxykanamycin B

6'-N-tert-butoxycarbonyl-3',4'-dideoxykanamycin B (111 mg, 0.2 millimoles) was dissolved in a mixture (4 ml) of pyridine-water-triethylamine (10:10:1 by volume), to which was added tert-butoxycarbonyl azide (32 mg, 0.22 millimoles). After stirring for 23 hours, the reaction mixture was concentrated to dryness under reduced pressure. The residue, without being purified, was dissolved in a mixture of water (2 ml) and dimethoxyethane (2 ml) and to the resulting solution was added a solution of 66 mg (0.22 millimoles) of N-hydroxysuccinimide ester of tert-butoxycarbonyl-L-isoserine in 1 ml of dimethoxyethane. The admixture was subsequently processed in the same manner as in Example 2 (b), affording 1-N-L-isoseryl-3',4'-dideoxykanamycin B in a 19% yield. Decomposition point 184°–186°C.

EXAMPLE 11

Synthesis of 1-N-D-isoseryl-3',4'-dideoxykanamycin B

Butoxycarbonylation of 6'-N-tert-butoxycarbonyl-3',4'-dideoxykanamycin B with tert-butoxycarbonyl azide, acylation with N-hydroxysuccinimide ester of tert-butoxycarbonyl-D-isoserine, removal of tert-butoxycarbonyl groups and column chromatography in the same manner as in Example 2 (b) afforded 1-N-D-isoseryl-3',4'-dideoxykanamycin B in a 18% yield. Decomposition point 184°–187°C.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope of this invention, can make various changes and modifications of this invention to adapt it to various usage conditions.

What we claim is:

1. A compound selected from the group consisting of 1-N-isoserylkanamycin; 1-N-isoserylkanamycin B; 1-N-isoseryl-3',4'-dideoxykanamycin B; and the pharmaceutically acceptable acid-addition salts thereof.
2. A compound as claimed in claim 1, 1-N-DL-isoserylkanamycin.
3. A compound as claimed in claim 1, 1-N-L-isoserylkanamycin.
4. A compound as claimed in claim 1, 1-N-D-isoserylkanamycin.
5. A compound as claimed in claim 1, 1-N-DL-isoserylkanamycin B.
6. A compound as claimed in claim 1, 1-N-L-isoserylkanamycin B.
7. A compound as claimed in claim 1, 1-N-D-isoserylkanamycin B.
8. A compound as claimed in claim 1, 1-N-DL-isoseryl-3',4'-dideoxykanamycin B.
9. A compound as claimed in claim 1, 1-N-L-isoseryl-3',4'-dideoxykanamycin B.
10. A compound as claimed in claim 1, 1-N-D-isoseryl-3',4'-dideoxykanamycin B.
11. A process for preparing a compound as claimed in claim 1, which comprises:
    a. reacting
        i. a starting compound selected from the group consisting of 6'-N-tert-butoxycarbonylkanamycin; 6'-N-benzyloxycarbonylkanamycin; 2',6'-di-N-tert-butoxycarbonylkanamycin B; 2',6'-di-N-tert-butoxycarbonyl-3',4'-dideoxykanamycin B; or 2'-N-tert-butoxycarbonyl-6'-N-benzyloxycarbonyl-3',4'-dideoxykanamycin B with
        ii. the N-hydroxysuccinimide ester of tert-butoxycarbonylisoserine or the N-hydroxysuccinimide ester of benzyloxycarbonyl isoserine to form a corresponding 1-N-monoisoseryl derivative of said starting compound; and
    b. reducing the 6'-N and 2'-N substituents on said 1-N-monoisoseryl derivative to amino groups to form said compound as claimed in claim 1.

* * * * *